(12) United States Patent
Franklin et al.

(10) Patent No.: US 7,048,991 B2
(45) Date of Patent: May 23, 2006

(54) ELASTIC COMPOSITES FOR GARMENTS

(75) Inventors: Kent A. Franklin, Appleton, WI (US); Valerie V. Finch, Neenah, WI (US); Jon M. Verbruggen, Little Chute, WI (US); Robin K. Nason, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 5 days.

(21) Appl. No.: 10/872,745

(22) Filed: Jun. 21, 2004

(65) Prior Publication Data
US 2004/0230174 A1 Nov. 18, 2004

Related U.S. Application Data

(62) Division of application No. 10/029,375, filed on Dec. 20, 2001, now Pat. No. 6,890,630.

(51) Int. Cl.
*B32B 27/14* (2006.01)

(52) U.S. Cl. .................. 428/198; 428/152; 428/137; 442/401; 442/328; 442/394; 156/290; 156/324; 604/385.27

(58) Field of Classification Search ............... 428/152, 428/137, 141, 198, 131, 219, 500; 442/401, 442/318, 328, 394; 604/385.27; 156/290, 156/324
See application file for complete search history.

(56) References Cited

U.S. PATENT DOCUMENTS

| 4,371,417 A | 2/1983 | Frick et al. |
| 4,729,131 A | 3/1988 | Thygesen |
| 4,862,523 A | 9/1989 | Lipov |
| 4,880,420 A | 11/1989 | Pomparelli |
| 4,977,011 A | 12/1990 | Smith |
| 5,092,861 A | 3/1992 | Nomura et al. |
| 5,147,487 A | 9/1992 | Nomura et al. |
| 5,171,388 A | 12/1992 | Hoffman et al. |
| 5,209,801 A | 5/1993 | Smith |
| 5,213,645 A | 5/1993 | Nomura et al. |
| 5,221,390 A | 6/1993 | Persson et al. |
| 5,330,598 A | 7/1994 | Erdman et al. |
| 5,340,424 A | 8/1994 | Matsushita |
| 5,342,341 A | 8/1994 | Igaue et al. |
| 5,389,173 A | 2/1995 | Merkatoris et al. |
| 5,413,654 A | 5/1995 | Igaue et al. |

(Continued)

FOREIGN PATENT DOCUMENTS

DE 3423644 A1 2/1986

(Continued)

OTHER PUBLICATIONS

International Search PCT/US 02/20722, dated Mar. 19, 2004, 5 pages.

(Continued)

*Primary Examiner*—Merrick Dixon
(74) *Attorney, Agent, or Firm*—Senniger Powers

(57) ABSTRACT

An elastic composite is formed by securing an elastic member to a substrate along a securement path extending longitudinally of the substrate. The position of the elastic member on the substrate varies laterally along the longitudinally extending securement path in a generally periodic wave pattern having at least one period within the securement path. The periodic wave pattern is such that the elastic composite is more stretchable in the direction of the securement path than transverse to the securement path. In another embodiment, the securement path varies laterally as it extends longitudinally along the securement path. The position of the elastic member varies transversely within the securement path to at least partially define a width of the securement path.

14 Claims, 14 Drawing Sheets

U.S. PATENT DOCUMENTS

| | | |
|---|---|---|
| 5,415,649 A | 5/1995 | Watanabe et al. |
| 5,440,764 A | 8/1995 | Matsushita |
| 5,447,508 A | 9/1995 | Numano et al. |
| 5,449,353 A | 9/1995 | Watanabe et al. |
| 5,500,075 A | 3/1996 | Herrmann |
| 5,517,832 A | 5/1996 | Kristensen |
| 5,525,175 A | 6/1996 | Blenke et al. |
| 5,531,850 A * | 7/1996 | Herrmann .................. 156/161 |
| 5,569,227 A | 10/1996 | Vandemoortele et al. |
| 5,576,091 A | 11/1996 | Zajaczkowski et al. |
| 5,634,917 A | 6/1997 | Fujioka et al. |
| 5,643,396 A | 7/1997 | Rajala et al. |
| 5,660,664 A | 8/1997 | Herrmann |
| 5,749,865 A | 5/1998 | Yamamoto et al. |
| 5,766,411 A | 6/1998 | Wilson |
| 5,779,689 A | 7/1998 | Pfeifer et al. |
| 5,814,036 A | 9/1998 | Rönnberg et al. |
| 5,830,203 A | 11/1998 | Suzuki et al. |
| 5,836,931 A | 11/1998 | Toyoda et al. |
| 5,855,573 A | 1/1999 | Johansson |
| 5,985,070 A | 11/1999 | Boberg |
| 6,013,065 A | 1/2000 | Suzuki et al. |
| 6,077,254 A | 6/2000 | Silwanowicz et al. |
| 6,129,720 A | 10/2000 | Blenke et al. |
| 6,179,946 B1 | 1/2001 | Ward et al. |
| 6,197,406 B1 | 3/2001 | Kwok |
| 6,210,387 B1 | 4/2001 | Rudberg et al. |
| RE37,154 E | 5/2001 | Nomura et al. |
| 6,468,630 B1 | 10/2002 | Mishima et al. |
| 6,475,600 B1 * | 11/2002 | Morman et al. ............ 428/152 |
| 6,585,841 B1 | 7/2003 | Popp et al. |
| 6,608,236 B1 * | 8/2003 | Burnes et al. ............. 604/378 |

FOREIGN PATENT DOCUMENTS

| | | |
|---|---|---|
| EP | 0 172 037 B1 | 2/1986 |
| EP | 0 626 160 B1 | 11/1994 |
| EP | 0 626 161 B1 | 11/1994 |
| EP | 0 694 297 A1 | 1/1996 |
| EP | 0 800 367 B1 | 10/1997 |
| JP | 06 070 958 | 3/1994 |
| JP | 07 117 125 | 5/1995 |
| JP | 11 062 805 | 3/1999 |
| WO | WO 90/04374 A1 | 5/1990 |
| WO | WO 90/09159 A1 | 8/1990 |
| WO | WO 94/01070 A1 | 1/1994 |
| WO | WO 95/28902 A1 | 11/1995 |
| WO | WO 96/18366 A1 | 6/1996 |
| WO | WO 96/23464 A1 | 8/1996 |
| WO | WO 96/23466 A1 | 8/1996 |
| WO | WO 97/00654 A1 | 1/1997 |
| WO | WO 97/06299 A1 | 2/1997 |
| WO | WO 98/25767 A1 | 6/1998 |
| WO | WO 00/37003 A2 | 6/2000 |
| WO | WO 03/053318 A2 | 7/2003 |

OTHER PUBLICATIONS

International Search Report for PCT/US 02/20723 dated Nov. 28, 2002 (5 pages).

International Search Report for PCT/US 02/41454 dated Jul. 17, 2003 (6 pages).

* cited by examiner

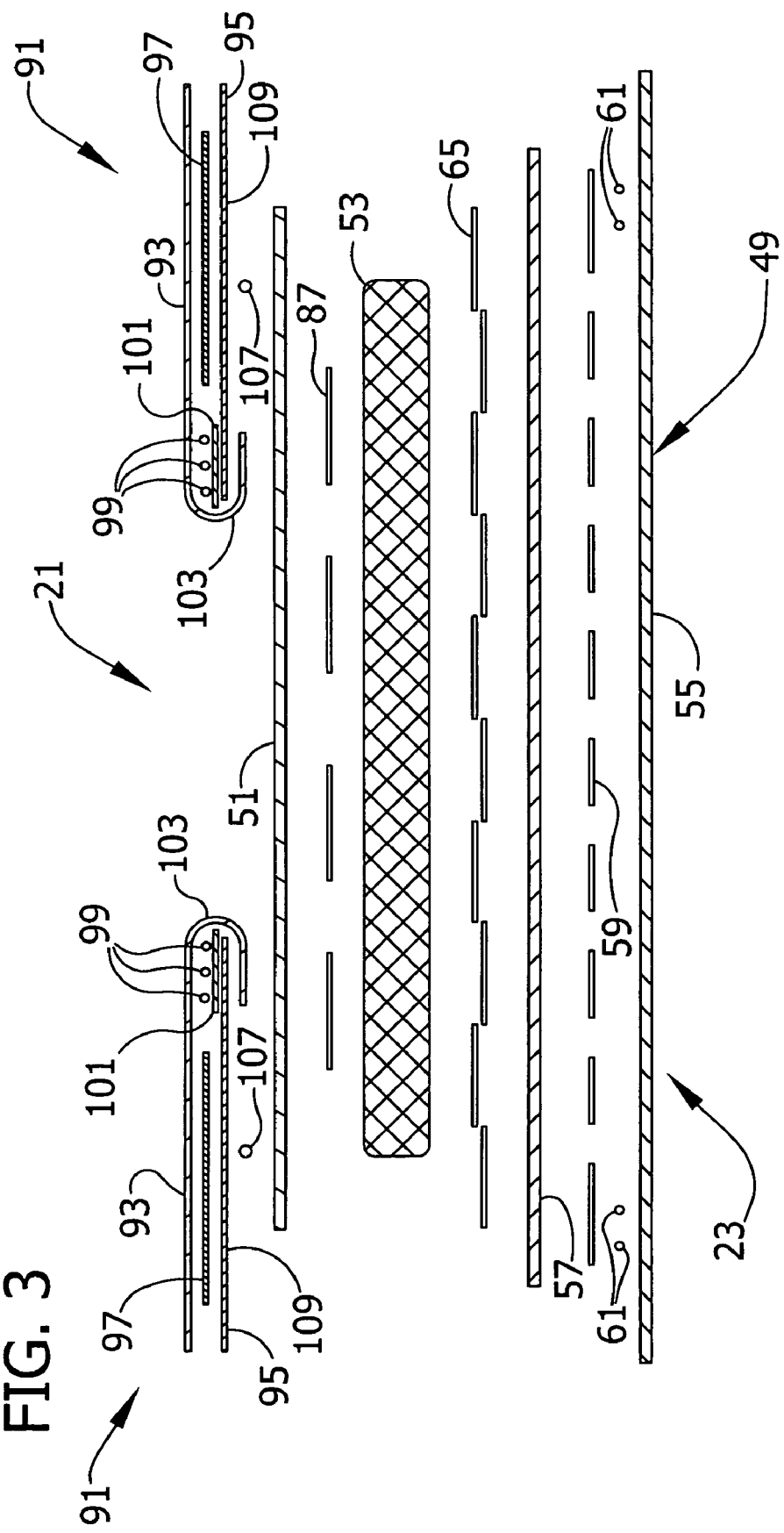

ELASTIC COMPOSITES FOR GARMENTS

CROSS-REFERENCE TO RELATED APPLICATION

This patent application is a divisional patent application of U.S. patent application Ser. No. 10/029,375 filed on Dec. 20, 2001, now U.S. Pat. No. 6,890,630, which is incorporated herein in its entirety.

BACKGROUND OF THE INVENTION

The present invention relates to garments having elastic components therein, and more particularly to elastic composites formed within such garments, or formed separately from such garments and secured therein, to provide an elastic component to such garments.

Garments such as conventional clothing items as well as disposable absorbent articles often have elastic composites formed or incorporated therein which permit stretching and provide retractive forces to certain portions of the garment to provide a snug but comfortable fit for the wearer. Elastic composites also allow the garment to fit a greater range of wearer sizes. To form the elastic composite, one or more elastic members, such as strands of elastic material, are typically secured to a substrate, such as a layer of the garment material, while in a stretched condition to thereafter apply a retractive force to the substrate for gathering the substrate. The elastic composite may also be formed by securing one or more elastic members to a substrate separate from the garment, such as in the form of a strip, or ribbon. The elastic composite is then secured to the garment to incorporate the elastic composite therein.

Children's toilet training pants are one example of a garment which may incorporate elastic composites. Training pants, which serve as a disposable training aid as a child transitions from diapers to underpants, are three-dimensional articles similar to underpants in appearance but constructed with a liquid permeable inner layer and an absorbent body to provide the absorbent function of a disposable absorbent article. Elastic members in the form of elastic strands are secured within the toilet training pants at the leg openings and sometimes in other areas of the training pants such as the waist opening and, if present, along containment flaps of the pants. The strands are adhered to a layer, or more typically between two layers, of the training pants, such as along the sides of the training pants adjacent the leg openings. The strands are secured within pants while in a stretched condition (e.g., in tension) so that the retractive force of the strands gathers the pants at the leg openings to provide a snug fit around the wearer's legs.

However, despite the benefits of forming or incorporating elastic composites into garments, there continues to be a need for improvements in the formation of such elastic composites. For example, there continues to be a need for increasing the comfort of such garments against the wearer's skin and for making a more efficient use of elastic members in disposable absorbent articles to thereby decrease the cost of manufacturing such articles.

SUMMARY OF THE INVENTION

In general, a disposable absorbent article of the present invention comprises a liner adapted for contiguous relation with the wearer's skin, an outer cover, and an absorbent body between the liner and the outer cover for absorbing liquid body waste. At least one elastic member is secured within the article along a generally crooked securement path. The position of the at least one elastic member varies transversely within the securement path to at least partially define a width of the securement path.

In another embodiment, the absorbent article comprises a liner adapted for contiguous relation with the wearer's skin, an outer cover, and an absorbent body between the liner and the outer cover for absorbing liquid body waste. At least one elastic member is secured within the article along a securement path. The position of the at least one elastic member varies transversely within the securement path in a generally periodic wave pattern having at least one period within the securement path. The periodic wave pattern is shaped such that said article is more stretchable in the direction of the securement path than transverse to the securement path.

In general, a method of the present invention for forming an elastic composite comprises moving a substrate in a flow direction thereof, guiding an elongate elastic member onto the substrate and securing the elastic member to the substrate. The guiding step comprises varying the lateral position of the elastic member relative to the flow direction of the substrate to vary the position of the elastic member transversely within the securement path in a generally periodic wave pattern. The periodic wave pattern is shaped such that the formed elastic composite is more stretchable in the direction of the securement path than transverse to the securement path.

In another embodiment, the method comprises moving a substrate in a flow direction thereof and guiding an elongate elastic member onto the substrate along a securement path. At least a portion of the securement path is oblique relative to the flow direction of the substrate. The guiding step comprises varying the lateral position of the elastic member relative to the flow direction of the substrate to vary the position of the elastic member transversely within the securement path. The elastic member is then secured to the substrate.

Other aspects and features of this invention will be in part apparent and in part pointed out hereinafter.

BRIEF DESCRIPTION OF THE DRAWINGS

FIG. 3 is a separated cross-section of the training pants of FIG. 1 taken laterally through a crotch region of the pants;

Corresponding reference characters indicate corresponding parts throughout the drawings.

DEFINITIONS

Figure 1:
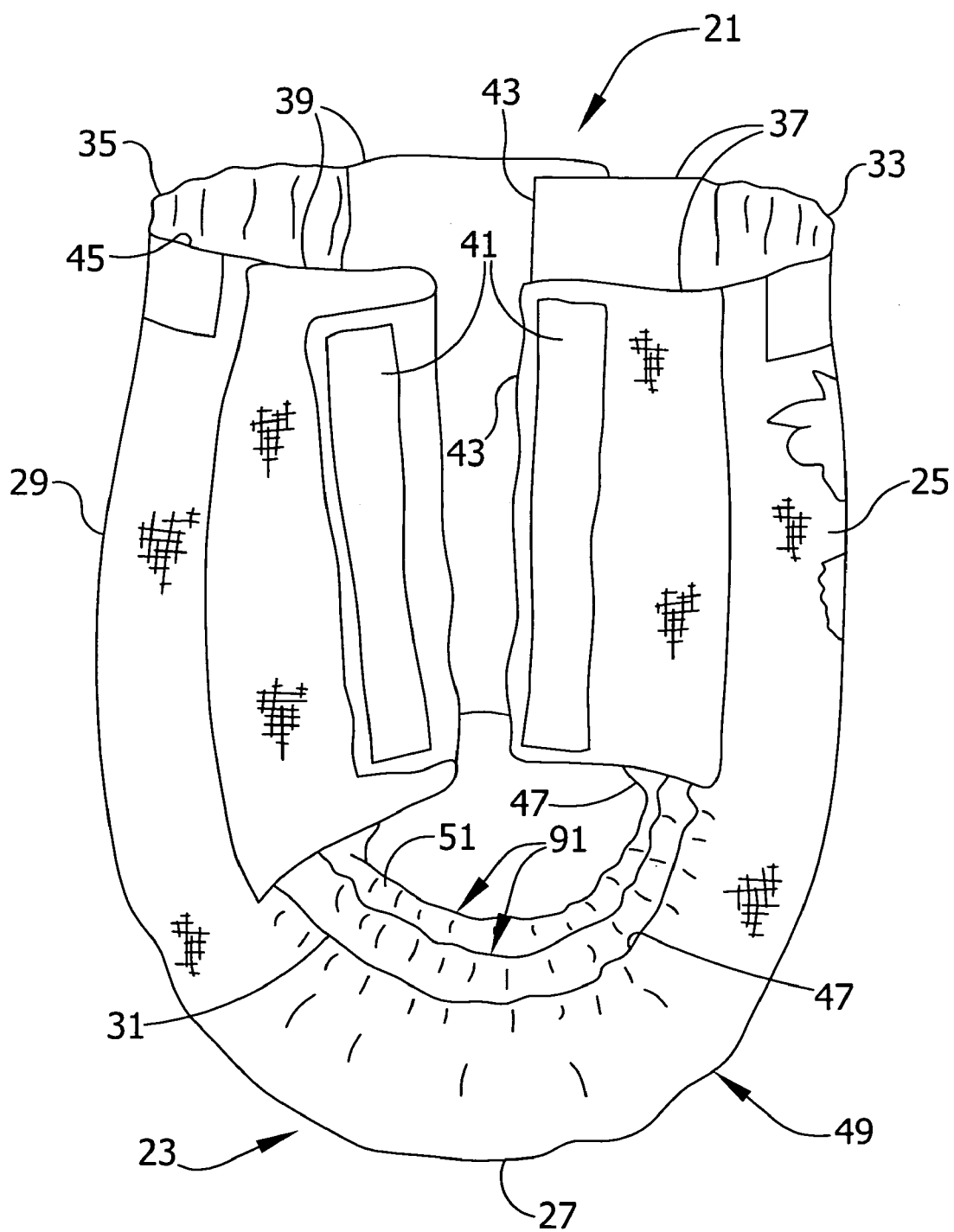
FIG. 1 is a side perspective of a children's toilet training pants.

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

(c) "Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

(d) "Layer" when used in the singular can have the dual meaning of a single element or a plurality of elements.

(e) "Liquid impermeable" when used in describing a layer or multi-layer laminate means that liquid body waste, such as urine, will not pass through the layer or laminate, under ordinary use conditions, in a direction generally perpendicular to the plane of the layer or laminate at the point of liquid contact.

(f) "Liquid permeable" refers to any material that is not liquid impermeable.

(g) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

(h) "Non-woven" and "non-woven web" refer to materials and webs of material which are formed without the aid of a textile weaving or knitting process.

(i) "Pliable" refers to materials which are compliant and which will readily conform to the general shape and contours of the wearer's body.

(j) "Spunbond" refers to small diameter fibers which are formed by extruding molten thermoplastic material as filaments from a plurality of fine capillaries of a spinnerette having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

(k) "Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

(l) "Thermoplastic" describes a material which softens when exposed to heat and which substantially returns to a non-softened condition when cooled to room temperature.

(m) "Three dimensional" refers to a garment similar to underwear, shorts or pants in that it has continuous leg and waist openings that are bounded by material of which the garment is made. The garment may or may not have manually tearable seams.

DETAILED DESCRIPTION OF THE PREFERRED EMBODIMENTS

Referring now to the drawings and in particular to FIG. 1, an elastic composite constructed in accordance with the present invention is shown and described herein with reference to a disposable absorbent article, and more particularly to a pair of children's toilet training pants, which is indicated in its entirety by the reference numeral 21. As used herein, a disposable absorbent article refers to an article which may be placed against or in proximity to the body (i.e., contiguous to the body) of the wearer to absorb and contain various liquid waste discharged from the body. Such articles are intended to be discarded after a limited period of use instead of being laundered or otherwise restored for reuse.

By way of illustration only, various materials and methods for constructing training pants 21 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 2:
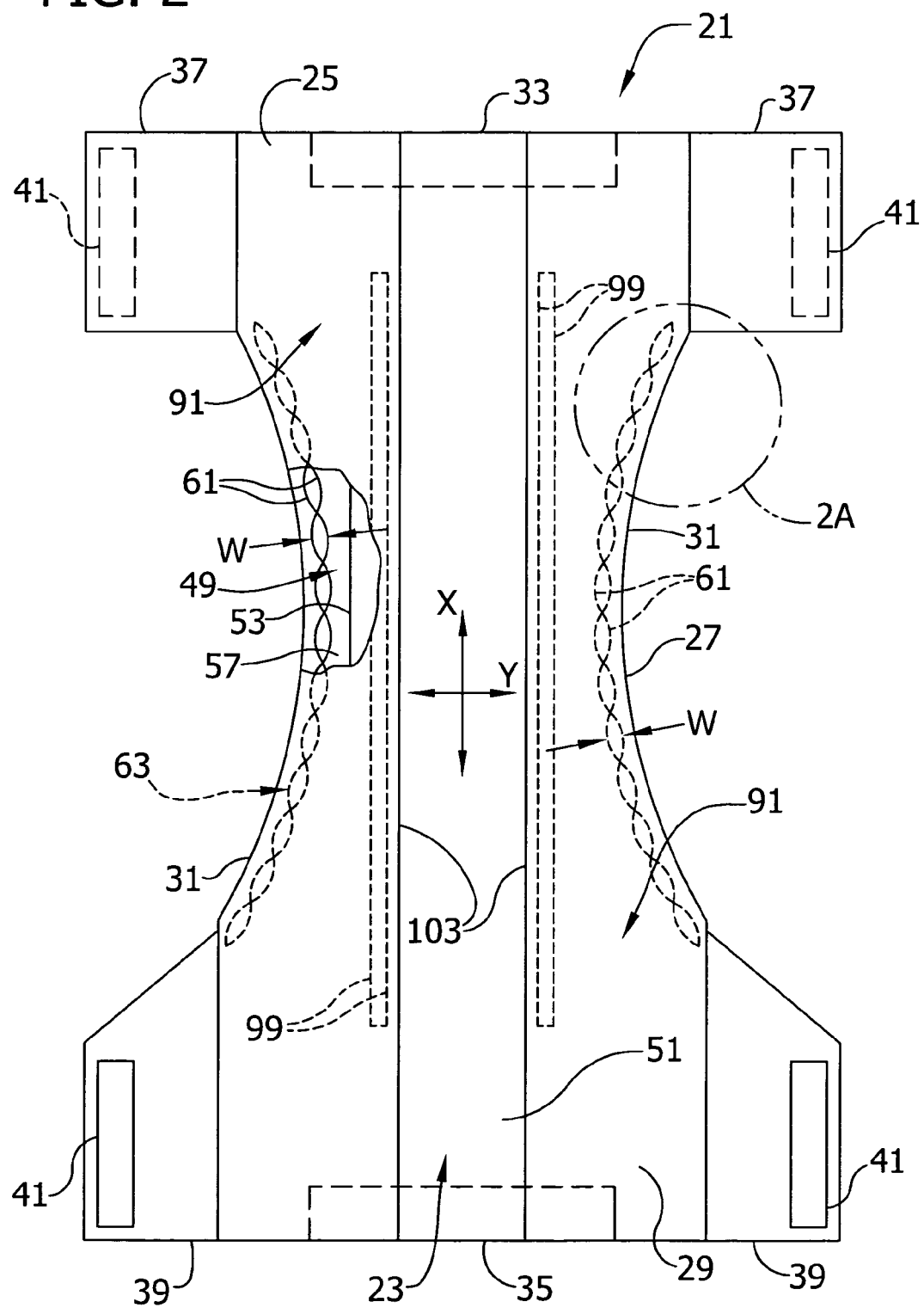
FIG. 2 is a top plan view of the training pants of FIG. 1 with the pants shown unfastened and laid flat and portions of the pants broken away to reveal an elastic composite of the present invention.

The training pants 21 of the illustrated embodiment have a longitudinal axis X and a lateral axis Y as indicated in FIG. 2 and generally comprise a central absorbent assembly 23 extending longitudinally from an anterior region 25 of the training pants through a crotch region 27 to a posterior region 29 of the training pants. The central absorbent assembly 23 is generally rectangular, and more particularly it is hourglass shaped, and has laterally opposite side edges 31 and longitudinally opposite front and rear waist edges or ends, respectively designated 33 and 35. As best seen in FIG. 2, the side edges 31 of the training pants 21 extend longitudinally from the anterior region through the crotch region to the posterior region for forming transversely spaced leg openings 47 (FIG. 1) of the training pants 21. Front and rear side panels 37, 39, respectively, are secured to the central absorbent assembly 23 as will be described later herein and extend laterally outward therefrom respectively at the anterior and posterior regions 25, 29 of the training pants 21.

To form the three-dimensional training pants 21, corresponding front and rear side panels 37, 39 (e.g., the front left side panel and the rear left side panel) are refastenably secured together, using fastening assemblies 41, along generally vertical seams 43. Alternatively, the front and rear side panels 37, 39 may be permanently secured together, such as by ultrasonic bonding, or they may be formed integrally with each other and/or with the central absorbent assembly 23. Securing the side panels 37, 39 together provides a central waist opening 45 and the transversely spaced leg openings 47 of the training pants 21. The training pants 21 are worn by inserting the wearer's feet through the waist opening 45 and the respective leg openings 47; grasping the training pants near the waist opening; and then pulling the pants up along the wearer's legs until the crotch region 27 of the training pants fits snugly against the crotch of the wearer.

With reference to FIG. 3, the central absorbent assembly 23 of the training pants 21 comprises an outer cover, generally indicated at 49, a bodyside liner 51 and an absorbent body 53 disposed between the outer cover and the liner. The outer cover 49 can be elastic, stretchable or non-stretchable and is desirably a multi-layered laminate structure of which at least one of the layers is liquid impermeable. For example, the outer cover 49 of the illustrated embodiment is of two-layer construction, including an outer layer 55 constructed of a liquid permeable material and an inner layer 57 constructed of a liquid impermeable material joined together by a laminate adhesive 59. It is understood that the outer cover 49 may instead be constructed of a single layer of impermeable material without departing from the scope of this invention.

The liquid permeable outer layer 55 of the outer cover 49 can be any suitable material and is desirably one which provides a generally cloth-like texture. One example of such a material is a 20 gsm (grams per square meter) spunbond polypropylene non-woven web. The outer layer 55 may also be constructed of the same materials from which the bodyside liner 51 is constructed as described later herein. Also, while it is not a necessity for the outer layer 55 of the outer cover 49 to be liquid permeable, it is desired that it provide a relatively cloth-like texture to the wearer.

The liquid impermeable inner layer 57 of the outer cover 49 can be either vapor permeable (i.e., "breathable") or vapor impermeable. The inner layer 57 is desirably manufactured from a thin plastic film, although other flexible liquid impermeable materials may also be used. The liquid impermeable inner layer 57 (or the liquid impermeable outer cover 49 where the outer cover is of a single-layer construction) inhibits liquid body waste from leaking out of the pants and wetting articles, such as bed sheets and clothing, as well as the wearer and care giver.

Leg elastic members 61 are secured between the outer and inner layers 55, 57 of the outer cover 49, such as by being bonded to one or both layers by the laminate adhesive 59. Thus it will be seen that the outer and inner layers 55, 57 of the outer cover 49 each broadly define a substrate to which the elastic members 61 may be secured to broadly form an elastic composite of the present invention. It understood that the leg elastic members 61 may be secured between the outer and inner layers 55, 57 of the outer cover 49 by adhesive (not shown) other than the laminate adhesive. It is also understood that the leg elastic members 61 may instead be secured between the outer cover 49 and the bodyside liner 51. In such a design, the leg elastic members 61 can be bonded to the outer cover 49, to the bodyside liner 51, or to both.

The elastic members 61 are desirably strands or threads of elastic material. However, as is well known to those skilled in the art, suitable elongate elastic members 61 also include sheets, ribbons of natural rubber, synthetic rubber, or thermoplastic elastomeric polymers. For example, one suitable elastic material from which the elastic members 61 may be constructed is a dry-spun coalesced multifilament elastomeric thread sold under the trade name LYCRA and available from E.I. du Pont de Nemours and Company, Wilmington, Del., U.S.A. The leg elastic members 61 are desirably secured between the outer and inner layers 55, 57 of the outer cover 49 while in a stretched (e.g., elastically contractible) condition such that retractive forces of the elastic members gather the training pants at the leg openings 47 to provide a snug fit around the wearer's legs. The elastic members 61 may also be colored to provide an aesthetic appearance to the pants 21.

Figure 2A:
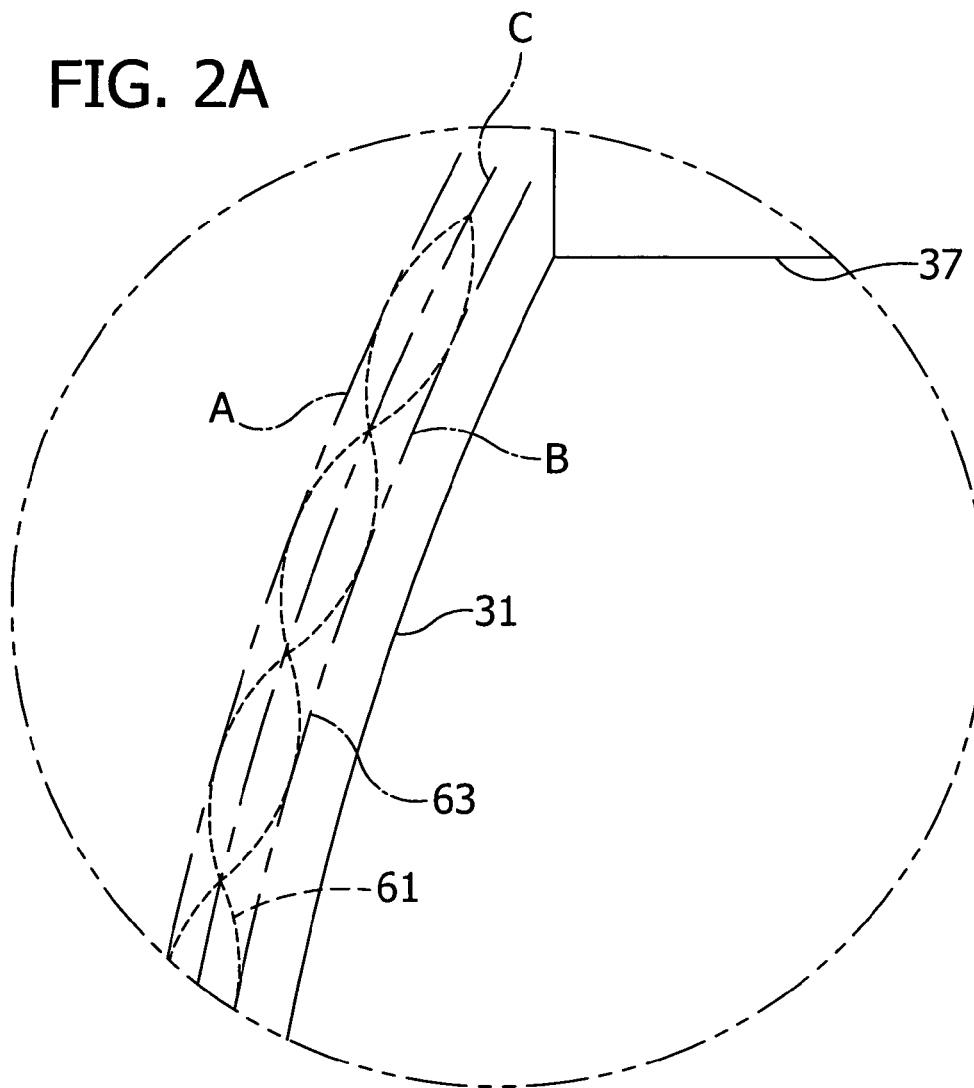
FIG. 2A is an enlarged view of a portion of the training pants of FIG. 2.
Figure 4A:
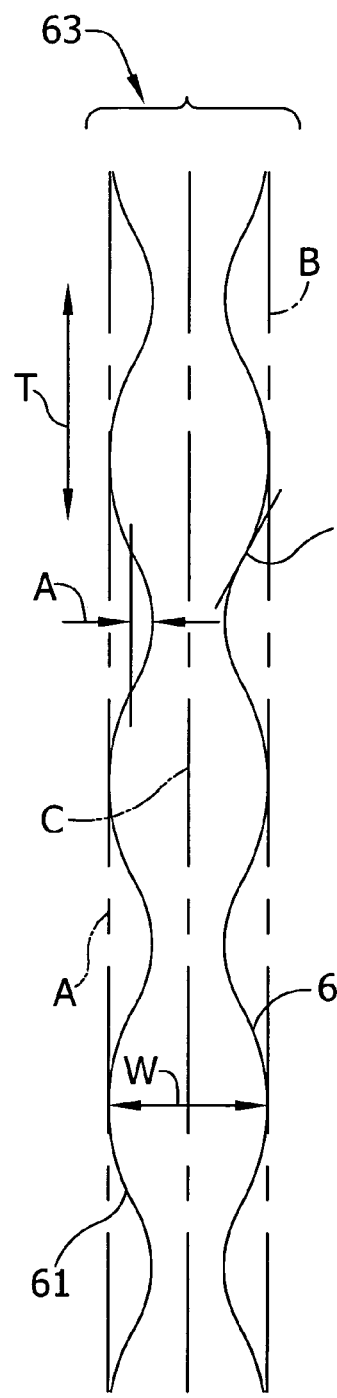
FIGS. 4A, 4B and 4C are schematics of various patterns that may be defined by elastic members of the elastic composite of the present invention.
Figure 4B:
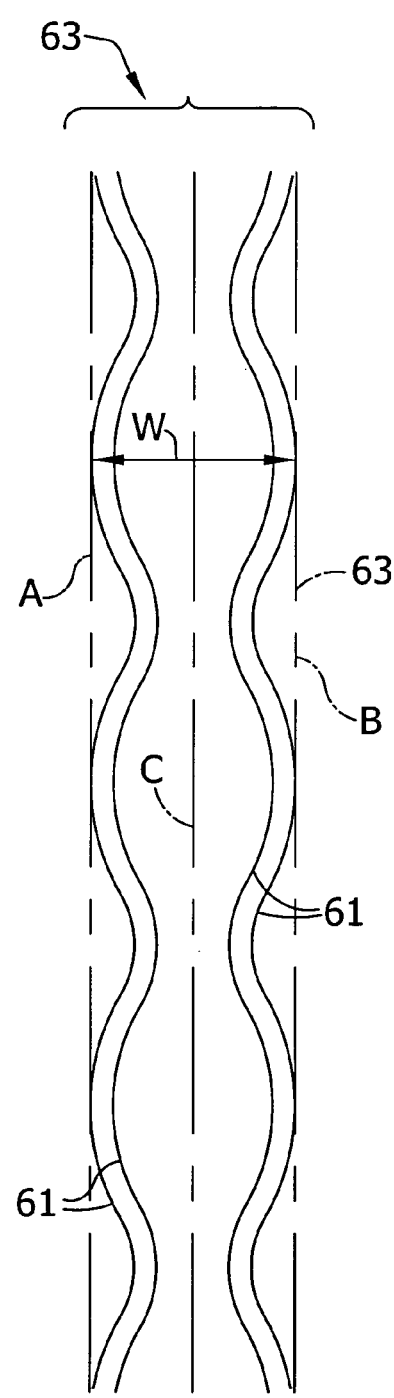
Figure 4C:
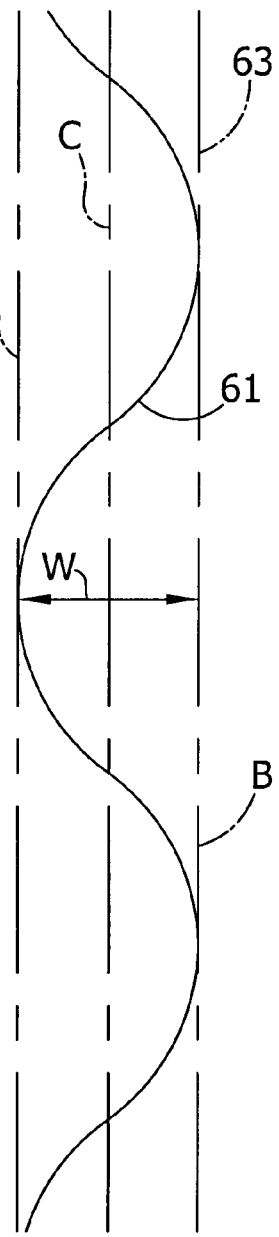

With reference to FIGS. 2 and 2A, the elastic members 61 are secured within the training pants 21 along respective securement paths, generally indicated at 63, extending longitudinally adjacent the laterally opposite side edges 31 of the training pants 21. The position of each elastic member 61 varies transversely within the respective securement path 63. As used herein, the term securement path 63 refers to the path along which one or more elastic members 61 are adhered to a substrate. As seen best in FIG. 2A, the securement path 63 has a width W defined by edge boundaries A, B of the elastic members 61. For example, one edge boundary A passes generally through the maxima of one outermost elastic member and the other edge boundary B passes generally through the minima of the opposite outermost elastic member. A centerline C of the securement path 63 extends midway between the edge boundaries A, B of the securement path. Where the positions of the elastic members 61 do not vary transversely relative to the securement path, such as in conventional training pants, the edge boundaries A, B are substantially co-linear with the outermost elastic members.

Where only one elastic member 61 is applied to a substrate (e.g., as shown in FIG. 4C), one edge boundary A passes generally through the maxima defined by the transverse position of the elastic member relative to the securement path 63 and the other edge boundary B passes generally through the minima defined by the transverse position of the elastic member relative to the securement path. Where the position of the elastic member does not vary transversely relative to the securement path, the width W defined by a single elastic member would be substantially zero and the centerline C and edge boundaries A, B of the securement path would all be co-linear.

The securement path 63 of the illustrated embodiment of FIG. 2 is broadly referred to herein as being crooked in that it varies laterally as it extends longitudinally adjacent the side edges 31 of the training pants 21 generally oblique, or non-parallel to the longitudinal axis X of the training pants. For example, the securement path 63 desirably follows the contour of the side edges 31 of the training pants 21, such as in a curvilinear or arcuate path, although it is understood that the securement path 63 may not follow the contour of the side edges, and may even extend in parallel relation to the longitudinal axis of the pants 21. As used herein, the securement path 63 is also considered to be crooked if the centerline C and/or either one of the edge boundaries A, B of a portion of the securement path 63 is arcuate, bent or otherwise oblique relative to a particular axis, such as the longitudinal axis of the pants 21. Each leg elastic member 61 shown in FIG. 2 defines a generally periodic pattern, and more particularly a periodic wave pattern such as a sinusoidal pattern, along at least a portion of the securement path 63 of the elastic members. Desirably, at least two periods of the pattern are formed along the length of the securement path, e.g., within the training pants 21.

FIGS. 2, 4A, 4B, 4C and 5 are illustrative of a few patterns which can be defined by the elastic members 61 as they extend within the securement path 63. For example, FIG. 4A illustrates a pair of elastic members 61 defining two periodic wave patterns, each generally having an amplitude A and a period T, within the width W of the securement path 63. Preferably, at least one period T of the periodic wave pattern of each elastic member 61 is formed as the elastic member extends along the length of the securement path 63. The amplitude A and period T of the periodic wave pattern formed by each elastic member 61 are desirably formed such that the substrate to which the elastic member is bonded, e.g., the outer and inner layers 55, 57 of the outer cover 49, is more stretchable in the direction of the securement path 63 (e.g, generally tangential to the securement path) than in a generally transverse direction relative to the securement path. For example, a slope S defined by the change in the transverse position of each elastic member 61 within the securement path 63 as it extends in the direction of the securement path is desirably between about −1 and about 1. However, it is contemplated that the slope S may be greater than 1, or less than −1, and/or that the substrate to which the elastic member is secured is as stretchable, or more stretchable, in the transverse direction relative to the securement path 63 without departing from the scope of this invention.

The elastic members 61 shown in FIG. 4A generally have a constant and equal amplitude A and period T, with the periodic wave pattern of one elastic member being the negative of the other (e.g., 180E out of phase therewith) so that the transverse spacing between the elastic members varies within the securement path 63. The elastic members 61 are also sufficiently spaced so that they do not cross each other within the securement path 63. As in FIG. 4A, the periodic wave patterns of the elastic members 61 shown in FIG. 2 also have a substantially constant and equal amplitude and period throughout the securement path 63, and the periodic wave pattern defined by one elastic member is the negative of the periodic wave pattern defined by the other elastic member. The elastic members 61 of FIG. 2 are sufficiently close so that the elastic members periodically cross each other along the securement path 63.

FIG. 4B illustrates two pairs of elastic members 61 extending along the securement path 63. In this embodiment, each pair of elastic members 61 defines two periodic wave patterns having a substantially constant and equal amplitude and period, with the elastic members arranged in parallel, spaced relationship with each other along the securement path 63. The periodic wave patterns of one pair of elastic members 61 are the negative of the periodic wave patterns of the other pair of elastic members. FIG. 4C illustrates a single elastic member 61 defining the securement path 63.

Figure 5:
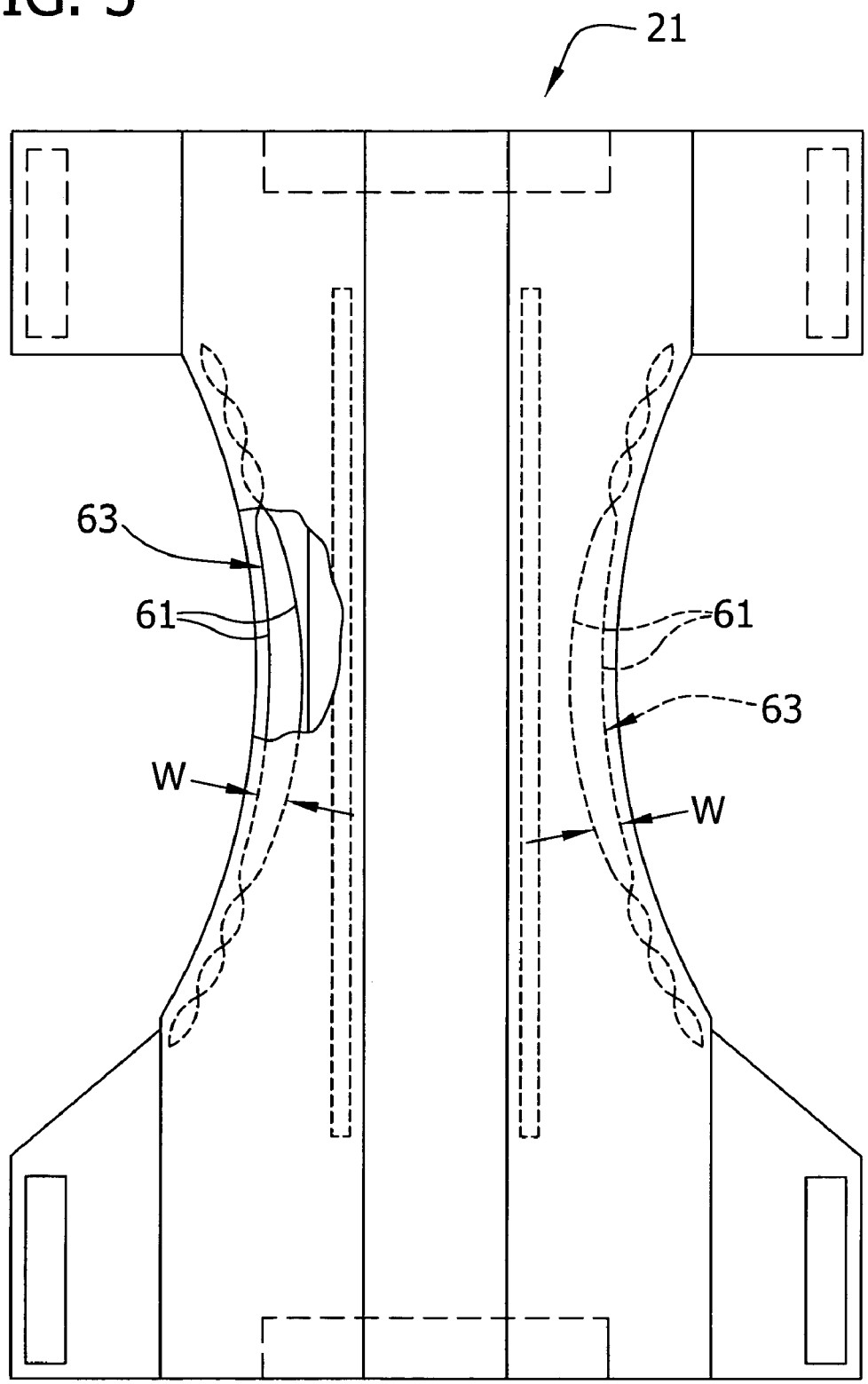
FIG. 5 is a top plan view of training pants similar to FIG. 2 illustrating a pattern that may be defined by leg elastic members of the training pants.

FIG. 5 illustrates training pants 21 having a pair of elastic members 61 similar to those shown in FIG. 2 extending along each of the securement paths 63 formed adjacent the leg openings 47 of the training pants 21. Along a segment of the securement path 63, the elastic members 61 extend along arcs having different radii such that the elastic members are spaced transversely from each other in non-parallel relationship, thereby varying the width W of the securement path.

It is contemplated that the pattern of one elastic member 61 may have a different amplitude and/or period than the pattern of the other elastic member, and the elastic members may be more closely or distantly spaced relative to each other than as shown in the illustrated embodiments, without departing from the scope of this invention. It is also understood that one elastic member 61 may not extend the full length of the securement path 63, or that only a single elastic member may extend along the securement path.

By securing the leg elastic members 61 between the outer and inner layers 55, 57 of the outer cover 49 in a generally periodic wave pattern within the securement path 63, the elastic members affect a substantially increased surface area of the outer cover in comparison to elastic members secured generally parallel to or otherwise co-linear with the securement path. As a result, the retractive forces of the elastic members 61 act against a greater surface area of the wearer's skin (i.e., a surface area roughly equal to the width of the securement path times its length), thereby increasing comfort to the wearer and reducing the risk that the elastic members will leave indentations or marks on the wearer. Also, because the elastic members 61 are spread over a wider surface area of the outer cover 49, a lesser number of elastic members may be needed to provide the desired fit of the pants 21 against the wearer's skin. For example, a pair of elastic members 61 formed in periodic wave patterns along the securement path 63 may replace three elastic members extending generally parallel to the securement path.

Referring back to FIG. 3, the absorbent body 53 is somewhat rectangular and is desirably constructed to be generally compressible, pliable, non-irritating to the wearer's skin and capable of absorbing and retaining liquid body waste, such as urine. The absorbent body 53 overlays the inner layer 57 of the outer cover 49, extending laterally between the leg elastic members 61, and is secured to the inner layer, such as by being bonded thereto with adhesive 65.

The bodyside liner 51 overlays the absorbent body 53 to isolate the wearer's skin from liquid body waste retained by the absorbent body and is secured to at least a portion of the absorbent body, such as by being bonded thereto with adhesive 87. The liner 51 further extends beyond the absorbent body 53 to overlay a portion of the inner layer 57 of the outer cover 49, particularly in the crotch region 27 of the pants 21, and is secured thereto, such as by being bonded thereto by adhesive 65, to substantially enclose the absorbent body between the outer cover and the liner about the periphery of the absorbent body. Although the bodyside liner 51 shown in FIG. 3 is slightly narrower than the outer cover 49, it is understood that the liner and outer cover may be of the same dimensions, or the liner may be sized larger than the outer cover, without departing from the scope of this invention. It is also contemplated that the liner 51 may not extend beyond the absorbent body 53 and may not be secured to the outer cover 49 and/or to the absorbent body 53. The bodyside liner 51 is desirably compliant, soft feeling, and non-irritating to the wearer's skin and can be less hydrophilic than the absorbent body 53 to provide a relatively dry surface to the wearer and permit liquid body waste to readily penetrate through its thickness.

The bodyside liner 51 can be manufactured from a wide selection of web materials, such as synthetic fibers (e.g., polyester or polypropylene fibers), natural fibers (e.g., wood or cotton fibers), a combination of natural and synthetic fibers, porous foams, reticulated foams, apertured plastic films, or the like. Various woven and non-woven fabrics can be used for the bodyside liner 51. For example, the liner 51 can be composed of a meltblown or spunbonded web of polyolefin fibers. Alternatively, the liner 51 can be a bonded-carded web composed of natural and/or synthetic fibers. The bodyside liner 51 can also be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL N-62 available from Uniqema, Inc., a division of ICI of New Castle, Del., U.S.A, and GLUCOPON 220UP available from Cognis Corporation of Ambler, Pa., U.S.A, in an active ratio of 3:1. The surfactant can be applied by any conventional means, such as spraying, printing, brush coating or the like. The surfactant can be applied to the entire liner 51 or it can be selectively applied to particular sections of the liner.

A particularly suitable bodyside liner 51 is constructed of a non-woven bicomponent web having a basis weight of about 27 gsm. The non-woven bicomponent can be a spun-bonded bicomponent web, or a bonded-carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Fibers having other orientations, such as multi-lobe, side-by-side, end-to-end may be used without departing from the scope of the invention. Also, although the outer cover 49 and bodyside liner 51 of the central absorbent assembly 23 can include elastomeric materials, it is contemplated that the central absorbent assembly may instead be generally inelastic, wherein the outer cover, the bodyside liner and the absorbent body 53 are composed of materials which are generally non-elastomeric.

The front and rear side panels 37, 39 of the training pants 21 may be bonded to the central absorbent assembly 23 at the respective anterior and posterior regions 25, 29 of the pants and extend outward beyond the laterally opposite edges 31 of the assembly. For example, the front side panels 37 of the illustrated embodiment are secured to the inner layer 57 of the outer cover 49, such as by being bonded thereto by adhesive (not shown), by thermal bonding or by ultrasonic bonding. These side panels 37 may also be secured to the outer layer 55 of the outer cover 49, such as by being bonded thereto by adhesive (not shown), by thermal bonding or by ultrasonic bonding. The rear side panels 39 are secured to the outer and inner layers 55, 57 of the outer cover 49, at the posterior region 29 of the training pants 21, in substantially the same manner as the front side panels 37. Alternatively, the side panels 37, 39 may be formed integrally with the central absorbent assembly 23, such as by being formed integrally with the outer cover 49, the bodyside liner 51 or other layers of the pants 21.

Containment flaps, generally indicated at 91, are secured to the bodyside liner 51 in generally parallel, spaced relation with each other laterally inward of the leg openings 47 to provide a barrier against the flow of urine to the leg openings. The containment flaps 91 extend longitudinally from the anterior region 25 of the training pants 21, through the crotch region 27 to the posterior region 29 of the pants. Each containment flap 91 comprises a non-woven layer 93 and a film layer 95 secured to the non-woven layer, such as by being bonded thereto by adhesive 97. Flap elastic members 99 are secured by suitable adhesive 101 between the non-woven layer 93 and the film layer 95 generally at a distal end 103 of the flap 91, with the non-woven layer 93 being folded over the flap elastic members 99 and the film layer 95 at the distal end 103. The flap 91 is secured to the bodyside liner 51 by a seam of adhesive 107 to define a proximal end 109 of the flap.

The flap elastic members 99 of the illustrated embodiment comprise three individual strands of elastomeric material extending longitudinally along the distal end 103 of the flap 91 in generally parallel, spaced relation with each other. One suitable elastic strand is a LYCRA T151 940 decitex elastic which can be obtained from E. I. du Pont de Nemours Co. of Wilmington, Del. The elastic strands are secured between the non-woven layer 93 and the film layer 95 while in an elastically contractible condition such that contraction of the strands gathers and shortens the distal end 103 of the containment flap 91. As a result, the elastic strands bias the distal end 103 of each flap 91 toward a position spaced from the proximal end 109 of the flap so that the flap extends away from the liner 51 in a generally upright orientation of the flap, especially in the crotch region 27 of the training pants 21, when the pants are fitted on the wearer. It is understood, however, that the containment flaps 91 may be omitted from the training pants 21 without departing from the scope of the invention.

While the elastic composite constructed in accordance with the present invention is shown and described above with particular reference to children's toilet training pants 21, and more specifically to the leg openings 47 of children's toilet training pants, it is understood that the elastic composite as referred to herein comprises any composite in which an elongate elastic member is applied to a flexible substrate, or between two such substrates, to provide retractive or stretching forces to the substrate in accordance with the present invention.

The substrate may be a film, woven fabric, knit fabric or non-woven fabric. Such fabrics may be of natural or synthetic fibers such as cotton, wool, polyester, nylon, polypropylene, polyethylene, or the like. The film may be of polyethylene, polyester, polyflourocarbons, polyimide, polypropylene, or the like. For example, the flap elastic members 99 of the training pants 21 of FIGS. 1–3 may be secured between the non-woven layer 93 and the film layer 95 of the flaps 91 in accordance with the elastic member patterns shown and described herein. Elastic members may also be secured to the training pants 21 at the front and rear waist edges 33, 35 thereof in accordance with the elastic member patterns shown and described herein.

The substrate may also be a generally continuous web, such as for forming multiple individual garments such as training pants whereby the web is cut into individual garments after the elastic members are secured to the web. In such an embodiment, the securement path 63 defines a pattern that is repeated once for each individual garment to be cut from the web.

It is contemplated that the elastic composite of the present invention may be formed or incorporated in various other garments. For example, other disposable absorbent articles, such as diapers and other infant and child care products, adult incontinence garments and other adult care products, sanitary napkins and other feminine care products and the like, as well as surgical bandages and sponges, may have one or more elastic members secured to one or more layers thereof in accordance with the present invention. Conventional garments such as pants, socks, shirts, hats, coats and the like may also have one or more elastic members secure to one or more layers thereof in accordance with the present invention. Alternatively, an elastic composite may be formed separately from a garment, such as in the form of an elastic strip or ribbon, and subsequently secured to a garment to provide an elastic component to the garment without departing from the scope of this invention.

FIGS. 6–11 illustrate an apparatus, generally indicated at 201, of the present invention for guiding one or more elastic members 61 (FIGS. 1–5) onto a substrate moving in a flow direction, indicated by the direction arrow F in the various figures, for securement to the substrate to form an elastic composite such as the training pants 21 of FIGS. 1–5. The apparatus 201 comprises a guide assembly, generally indicated at 203, which receives and guides one or more elastic members 61 onto the substrate, and a drive assembly, generally indicated at 205, which controls the position and operation of the guide assembly relative to the flow direction of the substrate. The drive assembly 205 comprises a base 207 secured against lateral movement relative to the flow direction of the substrate, and is desirably further secured against movement generally in the flow direction of the substrate. The base 207 of the illustrated embodiment is a generally rectangular plate constructed of plastic. However, the base 207 may have other configurations, such as a table, a box-shaped housing or other suitable configuration, and may be constructed of a material other than plastic, such as metal or wood.

Figure 6:
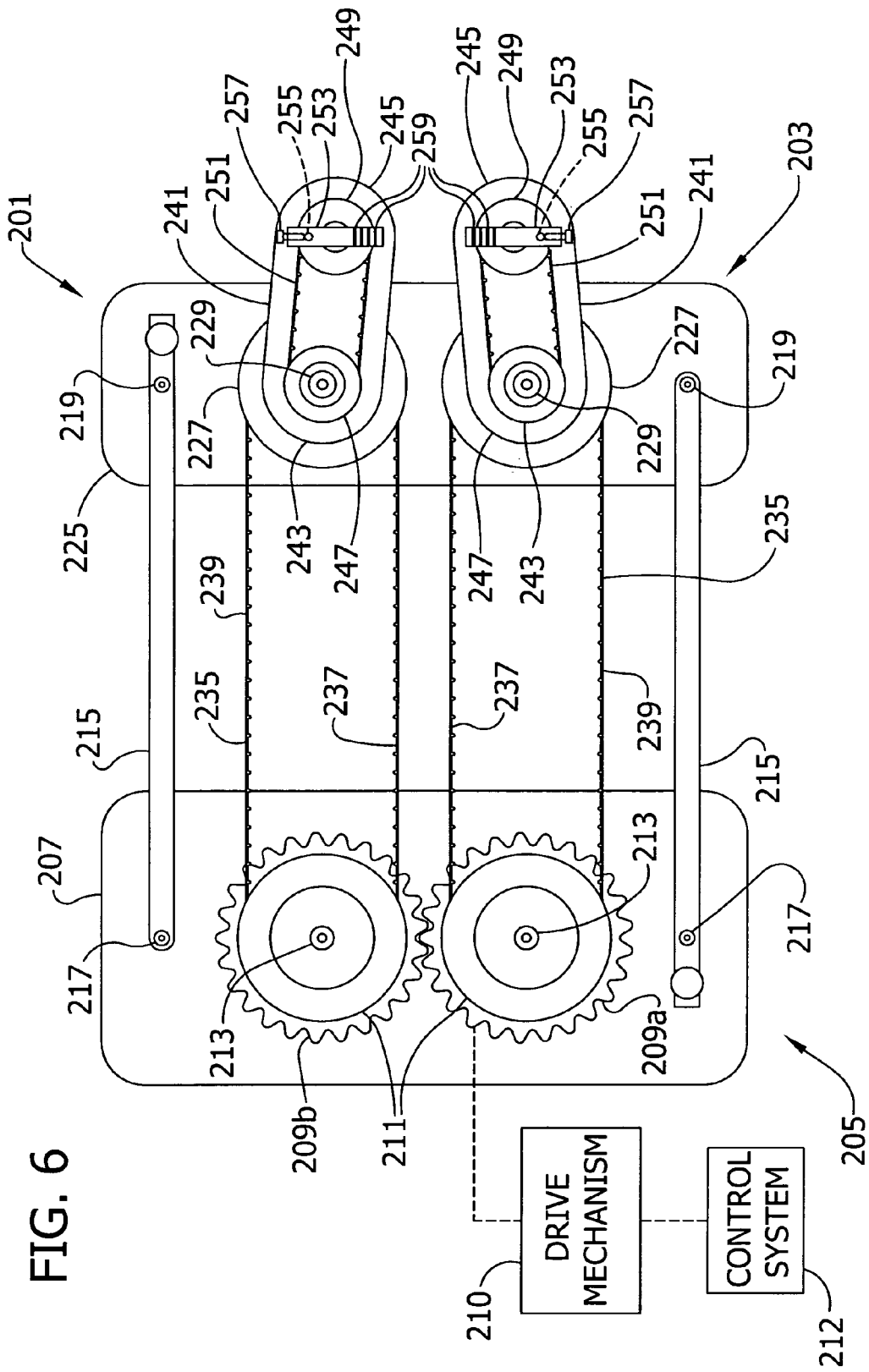
FIG. 6 is a diagrammatic top plan view of apparatus of the present invention for guiding one or more elastic members onto a substrate to form an elastic composite of the present invention.

Two gears 209a, 209b are rotatably mounted on the base 207 by respective fasteners 213 for rotation relative to the base about respective rotation axes of the gear fasteners. The gears 209a, 209b are interengaged so that rotation of one gear, e.g., clockwise, drives the other gear to rotate in a counter direction, e.g., counter-clockwise. As shown in FIG. 6, one gear 209a is desirably operatively connected, such as via a drive gear (not shown) or drive pulley (not shown) to a drive mechanism 210 (e.g., a motor) capable of driving rotation of the gear. The drive mechanism 210 is desirably controllable, such as by a suitable control system 212 to facilitate powered, controlled rotation (e.g., clockwise and/or counter-clockwise rotation) of the gears 209a, 209b relative to the base 207 in accordance with a pre-determined pattern to be formed by the elastic member(s) 61 guided onto the substrate. It is contemplated that the gears 209a, 209b may be out of engagement with each other, so that they may be rotated independently of each other either by a common drive mechanism or by separate drive mechanisms. It also contemplated that the drive assembly 205 may have only one gear or that the gears 209a, 209b may be omitted altogether without departing from the scope of this invention.

Figure 11:
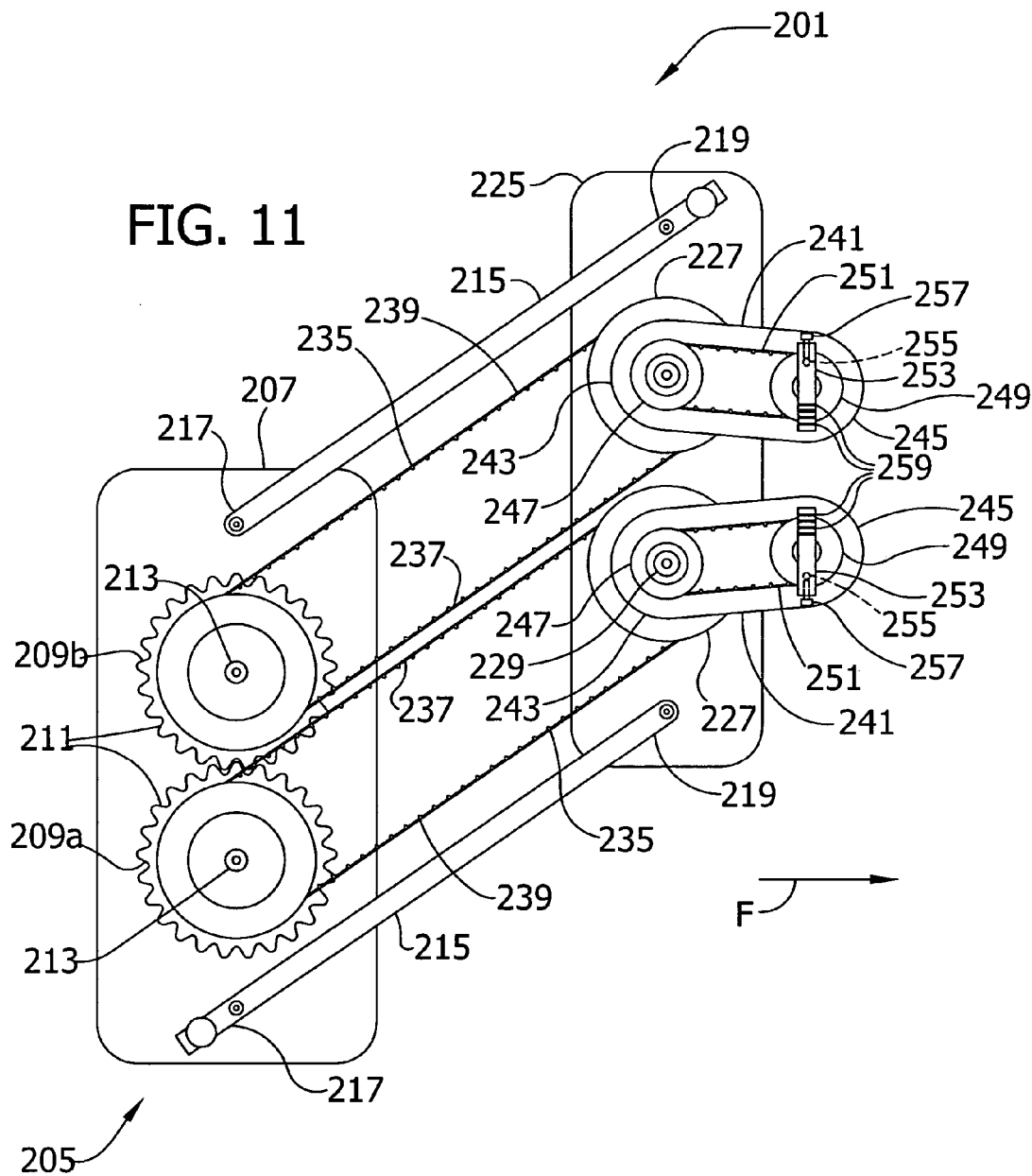
FIG. 11 is a top plan view of the apparatus of FIG. 6 with a guide assembly of the apparatus moved transverse to a drive assembly of the apparatus.

Pulleys 211 are seated on the gears 209a, 209b in coaxial relation therewith and secured by the respective gear fasteners 213 in engagement with the gears for conjoint rotation therewith about the respective rotation axes of the fasteners. Linkage comprising two linkage bars 215 is pivotally connected at one end 217 to the base 207 in parallel, spaced relation with each other for pivoting an opposite end 219 of the linkage bars 215 relative to the base to move the opposite end of the linkage bars generally laterally relative to the flow direction F of the substrate. The guide assembly 203 comprises a guide plate 225 pivotally connected to the opposite end 219 of the linkage bars 215 to permit lateral movement (e.g., as shown in FIG. 11) of the guide plate 225 relative to the base 207 and the flow direction F of the substrate while the angular orientation of the guide plate relative to the flow direction of the substrate remains generally constant. The guide plate 225 may be manually moved relative to the base 207 or, more desirably, it may be operatively connected to a drive mechanism (not shown) and corresponding control system (not shown) to permit powered, controlled movement of the guide plate relative to the base and the flow direction F of the substrate. It is contemplated that the linkage may instead comprise a single linkage bar pivotally connected at one end to the drive assembly and at its opposite end to the guide assembly 203 without departing from the scope of this invention.

The guide plate 225 of the illustrated embodiment is generally rectangular and is constructed of plastic. However, the guide plate 225 may have other configurations and it may be constructed of a material other than plastic, such as wood or metal, without departing from the scope of this invention. It is contemplated that the guide plate 225 may have an angular orientation relative to the flow direction F of the substrate other than the orientation shown in FIGS. 6–11, such as by being angled relative thereto. It is also contemplated that the guide plate 225 may not be connected to the base 207, or more generally to the drive assembly 203 so that the guide assembly may be moved relative to the flow direction of the substrate independent of the drive assembly, and that the guide assembly may instead be adapted for sliding movement transverse to the flow direction F of the substrate, without departing from the scope of this invention.

With particular reference to FIG. 6, the guide assembly 205 further comprises a pair of pulleys 227 corresponding to the drive assembly pulleys 211 mounted on the base 207. The pulleys 227 are rotatably mounted on the guide plate 225 by fasteners 229 for rotation relative to guide plate about the corresponding rotation axes of the fasteners. A spacer 231 (FIGS. 7 and 8) is secured by each fastener 229 between each guide assembly pulley 227 and the guide plate 225 to position the guide assembly pulleys above the guide plate at a level corresponding to the level of the drive assembly pulleys 211. The spacer 231 is desirably a bushing or a set of bearings, although other structure may be used as the spacer and remain within the scope of this invention. Continuous belts 235, having respective inner and outer reaches, respectively indicated at 237 and 239, are supported in tension by the corresponding guide assembly pulleys 227 and drive assembly pulleys 211 whereby rotation of the drive assembly pulleys rotates the guide assembly pulleys relative to the guide plate 225 in the same direction of rotation as the drive assembly pulleys. Desirably, the pulleys 211, 227 and belts 235 include interengaging teeth to inhibit slippage of the belts on the pulleys.

Where the drive assembly gears 209a, 209b are interengaged as in FIG. 1 for counter-rotation relative to each other, the guide assembly pulleys 227 rotate in counter directions upon rotation of the drive assembly gears. The lateral spacing between the guide assembly pulleys 227 is substantially the same as the lateral spacing between the drive assembly pulleys 211, and all of the pulleys are of the same size, so that the drive ratio of each drive assembly pulley to its corresponding guide assembly pulley is generally one to one. However, it is contemplated that the guide assembly pulleys 227 may instead be larger or smaller than the drive assembly pulleys 211 to obtain different drive ratios. It is also contemplated that the spacing between the guide assembly pulleys 227 may be greater or lesser than the spacing between the drive assembly pulleys without departing from the scope of this invention.

Each guide assembly pulley 227 has a positioning arm 241 mounted thereon generally at an inner end 243 of the positioning arm. The positioning arm 241 is held by the fastener 229 in engagement with the pulley 227 so that rotation of the pulley conjointly pivots the positioning arm about the rotation axis of the fastener. The positioning arm 241 extends radially out from the inner end 243 to an outer end 245 thereof which moves generally laterally relative to the flow direction F of the substrate as the positioning arm pivots about the rotation axis of the fastener 229. Inner (or first) and outer (or second) pulleys, indicated respectively at 247 and 249, are mounted on each positioning arm 241, with the inner pulley being located near the inner end of the positioning arm in coaxial relationship with the rotation axis of the fastener 229 and secured against rotation with respect to the arm about the fastener rotation axis. The outer pulley 249 is mounted on the positioning arm 241 in radially spaced relation with the inner pulley 247, such as near the outer end 245 of the positioning arm, for conjoint orbital movement with the outer end of the positioning arm relative to the guide plate 225 and the substrate about the rotation axis of the fastener 229 (and hence about the fixed, inner pulley). The outer pulley 249 is rotatable relative to the positioning arm 241 about a rotation axis of the outer pulley. A continuous belt 251 is supported in tension by the inner and outer pulleys 247, 249 so that orbital movement of the outer pulley about the fixed, inner pulley causes the outer pulley to rotate about its rotation axis relative to the positioning arm 241.

The outer pulley 249 has a guide 253 mounted thereon for receiving and guiding one or more elastic members 61 onto the substrate as the substrate is moved in its flow direction F. The guide 253 is mounted on the outer pulley 249 generally radially offset from the rotation axis thereof for orbital motion about the rotation axis of the outer pulley upon rotation of the pulley. Each guide 253 is mounted on the respective outer pulley 249 in a desired angular orientation relative to the flow direction F of the substrate, e.g., transverse thereto in the illustrated embodiment. The guides 253 shown in FIGS. 6–11 each comprise a rectangular block constructed of a transparent plastic material and mounted on the outer pulley 249 by a post 255 extending up from the pulley. A suitable fastener 257 extends laterally through each block to secure each block to the respective post 255 at an angular orientation relative to the flow direction F of the substrate. It is understood that the guide 253 may be constructed other than of plastic and may have a shape other than rectangular without departing from the scope of this invention. It is also contemplated that the guide 253 may be secured to the outer pulley 249 other than by a post 255 and/or fastener 257, such as by being permanently secured thereto, and remain within the scope of this invention.

The guides 253 each have a set of slots 259 formed therein. Each slot is sized for receiving one elastic member and guiding it onto the substrate. Instead of slots 259, the guides may have holes (not shown) formed therethrough without departing from the scope of this invention. It is also contemplated that instead of a block, the guides 253 may be in the form of an eyelet or other suitable form for receiving and guiding one or more elastic members 61 onto the substrate. While the guides 253 of the illustrated embodiment each have four slots 259 formed therein, the guides may have any number of slots, including one slot, depending on the number of elastic members 61 to be guided onto the substrate.

Also, while not shown in the drawings, the guides 253 may be mounted to the outer pulleys 243 at different heights relative to each other, such as by providing posts 255 of different lengths, or by using the fastener 257 to adjust the relative heights of, the guides on the posts. Positioning the guides 253 at different heights above the outer pulleys 249 provides sufficient clearance for using longer guides that generally cross above or below one another as they move transverse to the flow direction F of the substrate upon pivoting movement of the positioning arms 241 and corresponding rotation of the outer pulleys. In this manner, elastic members 61 guided onto the substrate by the guides 253 can cross each other within the securement path 63 of the elastic members as shown in FIG. 2.

It is also contemplated that the positioning arms 241 may be disposed at different heights relative to each other above the guide plate 225, or one positioning arm may be positioned above the guide plate and the other may be positioned below the guide plate, to provide sufficient clearance for the positioning arms to pivot up to 360E about the rotation axes of the fasteners 229. The outer pulleys 249 supporting the guides 253, and hence the guides themselves, are orbital relative to the substrate about the rotation axes of the fasteners through a generally circular path. In this manner, the drive mechanism may continuously rotate the drive assembly pulleys 209a, 209b through a full rotation to vary the transverse positions of the guides 253 relative to the flow direction F of the substrate, instead of oscillating the rotation of the pulleys back and forth through smaller rotations. The positioning arms 241 may also be of different lengths so that elastic the patterns formed by the elastic members 61 guided onto the substrate by the guides 253 have different amplitudes A.

Figure 7:
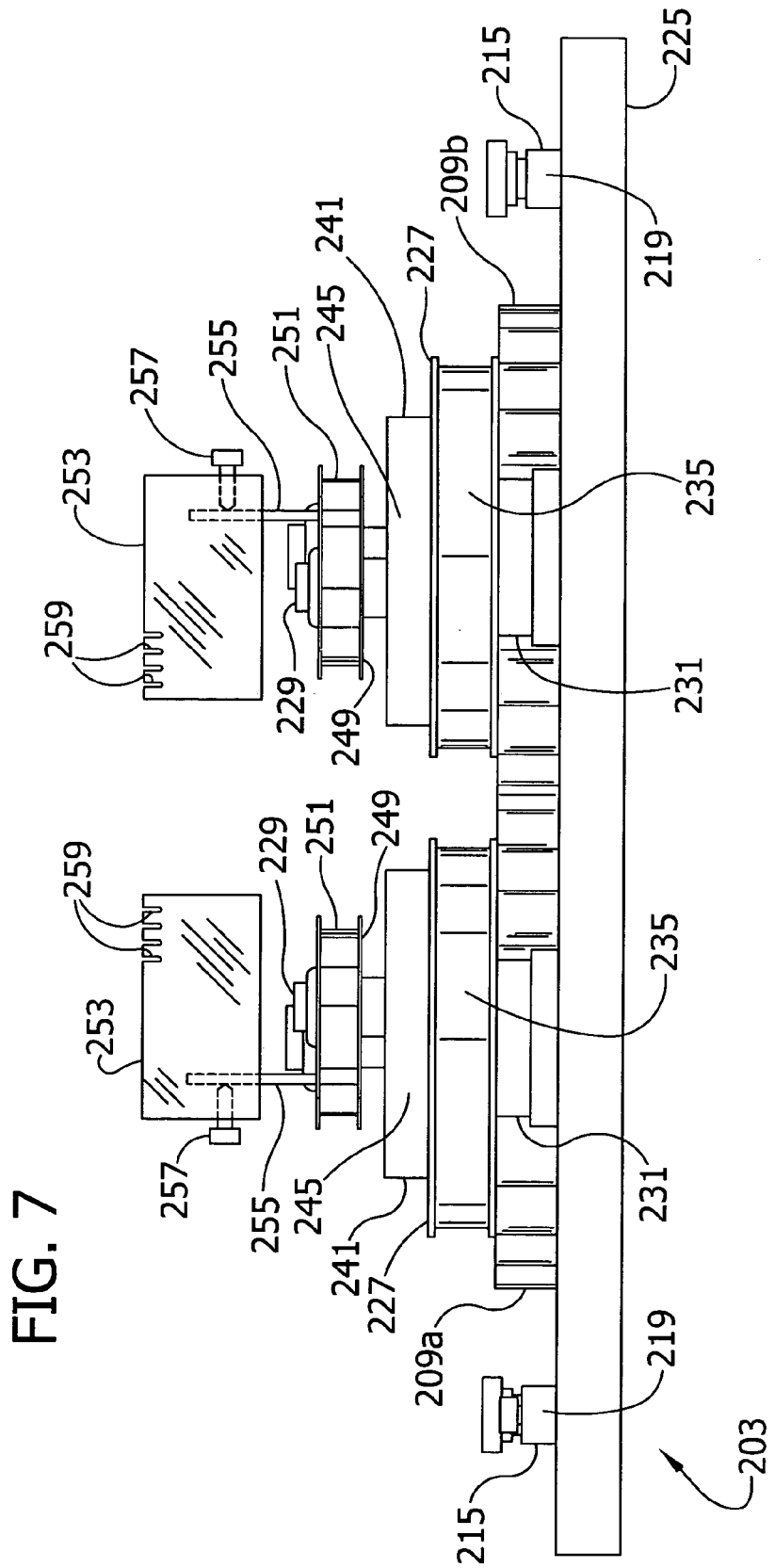
FIG. 7 is a front view thereof.
Figure 8:
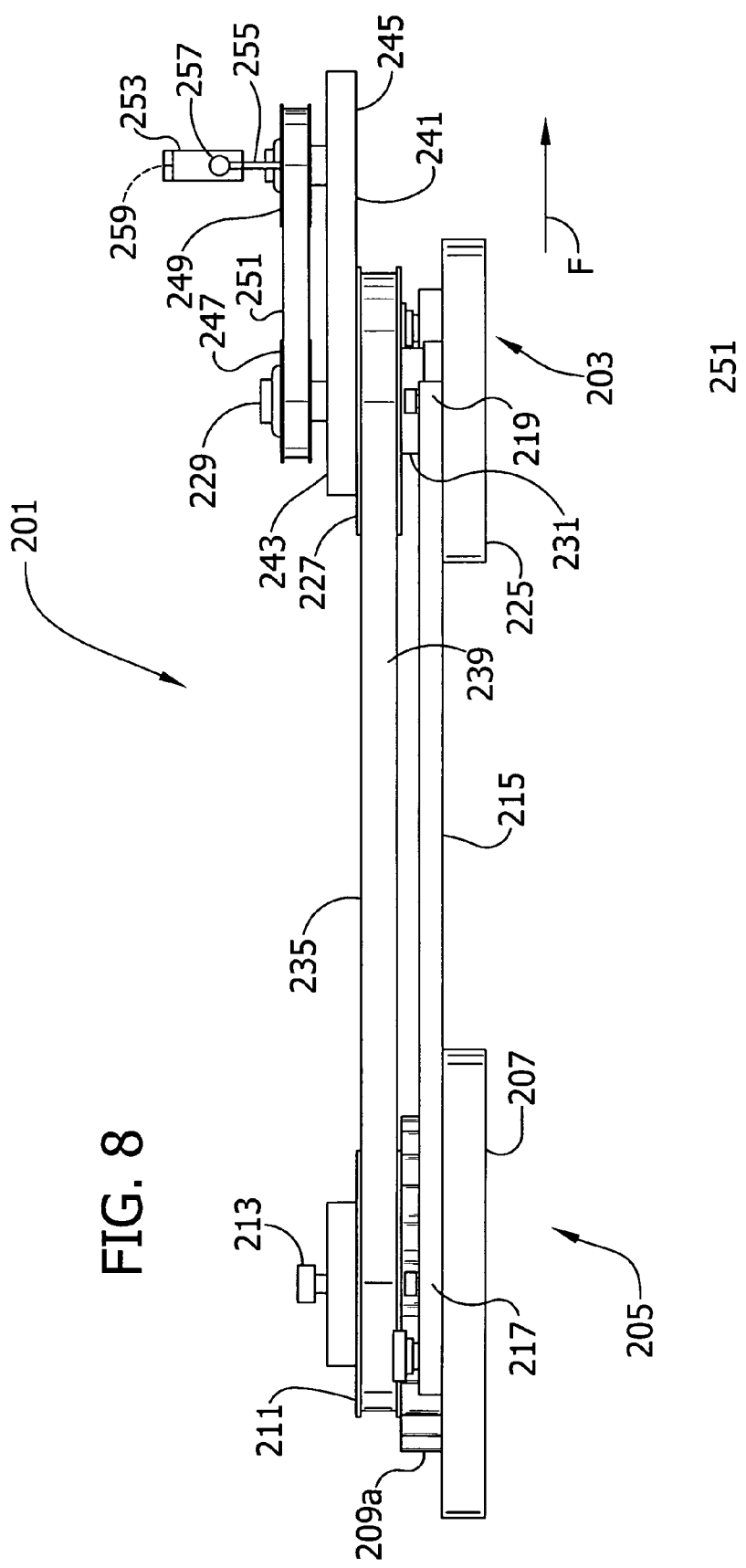
FIG. 8 is a side view thereof.

In operation of the apparatus 201 to guide an elastic member 61 onto a substrate moving in a flow direction F of the substrate (e.g., so as to form the periodic pattern of the elastic member on the substrate), the guide plate 225 is initially positioned at a desired transverse position relative to the base 207, such as in longitudinal relation therewith so that the linkage bars extend generally in the flow direction of the substrate as shown in FIGS. 6 and 7. The positioning arms 241 are also positioned at a desired angular position relative to the guide plate 225 and the flow direction F of the substrate, such as outward from the guide plate generally in the flow direction of the substrate as is also shown in FIGS. 6 and 7. It is understood, however, that the initial positions of the guide plate 225 and positioning arms 241 may be other than that shown in FIGS. 6 and 7 without departing from the scope of this invention. One or more elastic members 61 (FIGS. 2, 4A, 4B and 5) are received in the slots 259 of each guide 253 and directed therefrom onto the substrate for adherence to the substrate.

Figure 9:
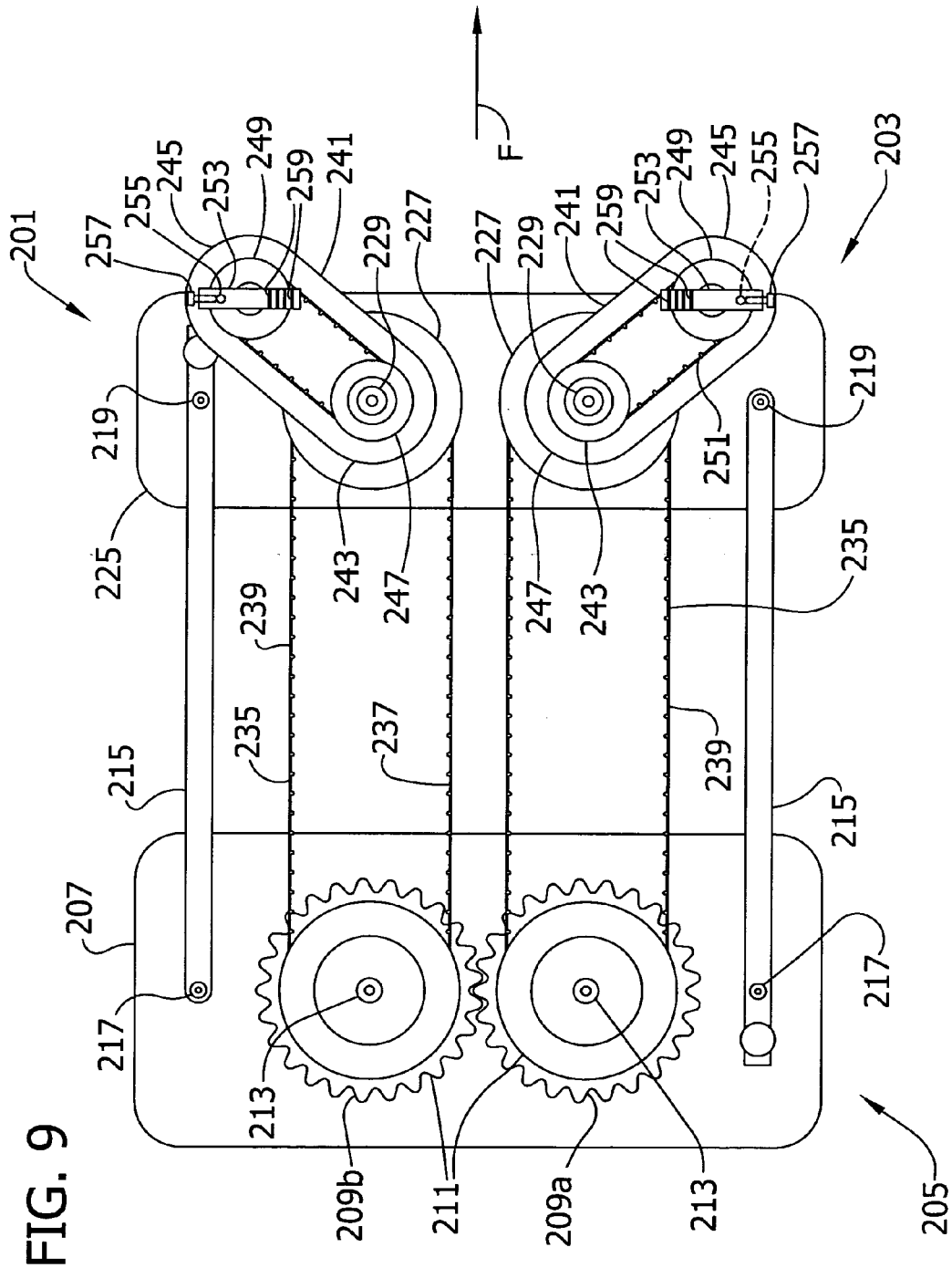
FIG. 9 is a top plan view of the apparatus of FIG. 6 with guides of the apparatus moved transversely outward relative to each other.
Figure 10:
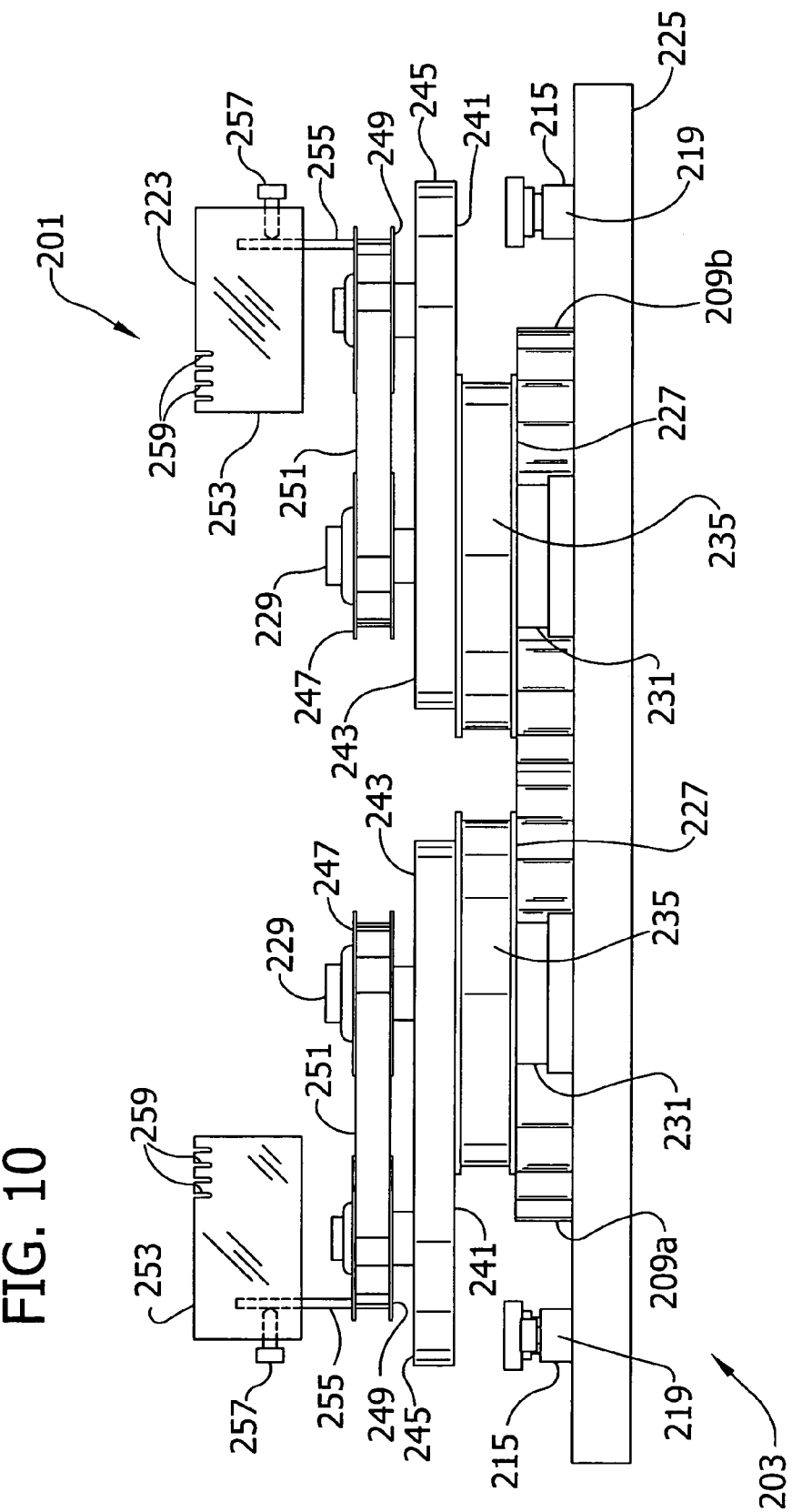
FIG. 10 is a front view thereof.

To vary the transverse position of the elastic members 61 relative to the flow direction F of the substrate while the securement path 63 remains generally parallel to the flow direction F of the substrate, one of the drive assembly gears, e.g., gear 209a (and hence the pulley 211 seated thereon) is rotated relative to the base 207, such as by the drive mechanism, in a desired direction of rotation, such as clockwise. The other gear 209b and pulley 211 are correspondingly rotated in a counter-clockwise direction. The guide assembly pulleys 227 are accordingly driven, via the continuous belts 251, in counter-rotating directions to pivot the positioning arms 241 about the respective rotation axes of the fasteners 229 in counter directions. For example, clockwise rotation of the drive assembly gear 209a effects pivoting of the positioning arms 241 to move generally out away from each other as shown in FIGS. 9 and 10.

Pivoting movement of the positioning arms 241 also effects orbital movement of each outer pulley 249 about its corresponding fixed, inner pulley 247 to effect lateral movement of the outer pulley and the guide 253 mounted thereon relative to the flow direction F of the substrate. As a result of the tension in the continuous belts 251 supported by the inner and outer pulleys 247, 249, the outer pulleys are rotated about their respective axes relative to the positioning arms 241. In turn, the guides 253 mounted on the outer pulleys 249 orbit about the respective rotation axes thereof, such as in a direction counter to the direction about which the positioning arm 241 is pivoted, so that the angular orientation of each guide relative to the flow direction F of the substrate remains substantially constant as the guides are moved laterally relative to the flow direction of the substrate. As shown in FIG. 11, to vary the securement path 63 laterally relative to the flow direction F of the substrate, the guide plate 225 is moved laterally relative to the base 207, and hence laterally relative to the flow direction of the substrate.

Figure 12:
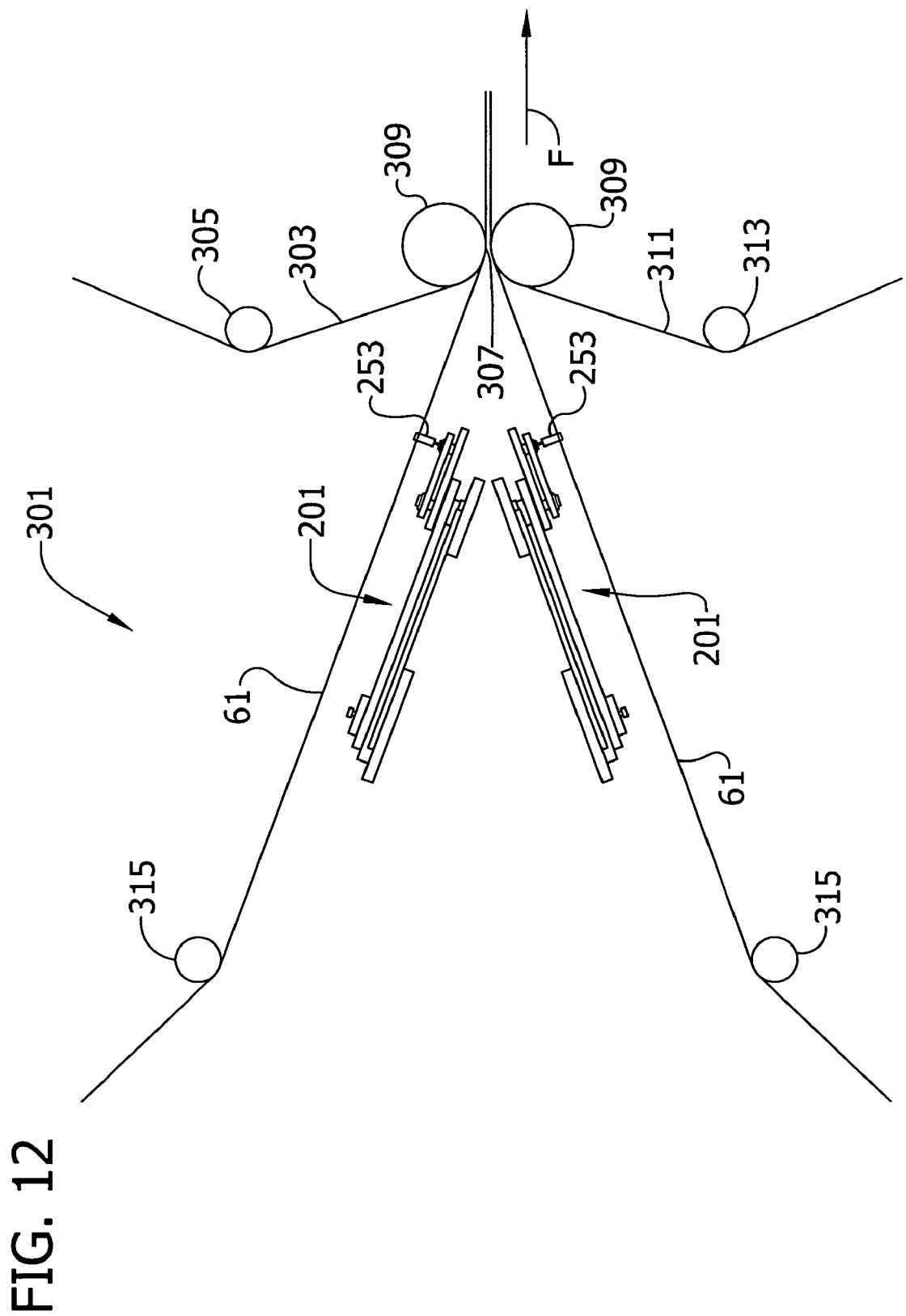
FIG. 12 is a schematic side view of a system of the present invention for applying a plurality of elastic members to children's toilet training pants.
Figure 13:
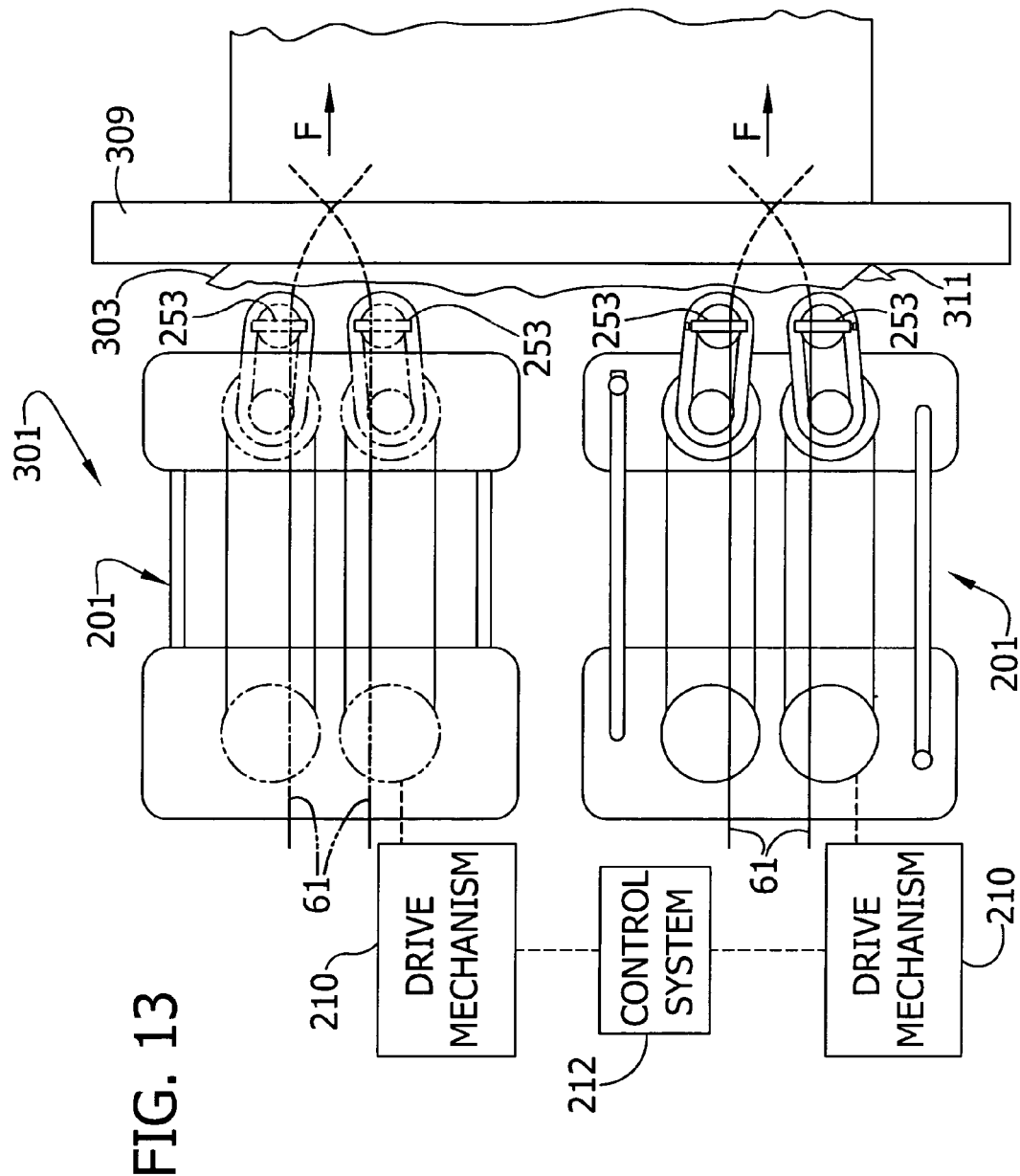
FIG. 13 is a schematic top plan view thereof.

FIGS. 12 and 13 illustrate a system, generally indicated at 301, of the present invention for applying one or more elongate members, such as elastic members 61 or inelastic members (not shown) to a substrate to form a composite, and more particularly for applying elastic members to disposable absorbent articles such as diapers or the training pants 21 of FIGS. 1–3 to form the elastic leg openings 47 thereof. The system 301 generally comprises a conveyance mechanism (not shown), such as a vacuum conveyor, for conveying a first substrate 303 (e.g., the inner layer 57 of the outer cover 49 of the training pants 21) from a source (not shown) of substrate material to pass over an idler roller 305 and then through a nip 307 defined by a pair of rollers 309 in a flow direction of the substrate material. A second conveyance mechanism (not shown), such as another vacuum conveyor, conveys a second substrate 311 (e.g., the outer layer 55 of the outer cover 49 of the training pants 21) to pass over another idler roller 313 and through the nip 307 in opposed relation with the first substrate 303. Adhesive (not shown) is desirably applied to the first substrate 303 and/or the second substrate 311, such as by spraying adhesive thereon, upstream from the nip 307. It is contemplated that as an alternative, or in addition to applying adhesive to one or both of the substrates 303, 311, adhesive may be applied to the elastic members 61 before the elastic members are adhered to the substrates or the elastic members may be self-adhering.

A pair of apparatus 201 of the present invention, e.g., for applying a pair of elastic members 61 to the pants 21, generally adjacent a respective one of the leg openings 47 of the pants, are positioned upstream of the nip 307 for guiding the elastic members onto the substrates 303, 311 before the substrates pass through the nip. The apparatus 201 are spaced laterally from each other (FIG. 13) and vertically from each other (FIG. 12) to provide sufficient clearance for pivoting movement of the positioning arms 241 of the apparatus. As best seen in FIG. 12, one apparatus 201 is inverted relative to the other apparatus. However, the apparatus 201 may both be upright, or they may both be inverted, and they may be at the same height or different heights, without departing from the scope of this invention. Elastic members 61, such as elastic strands, are pulled off of one or more unwinds (not shown) and around idler rollers 315 before being fed through the guides 253 (e.g., with one elastic member received in each guide) of each apparatus 201 for guiding the elastic members onto the substrates 303, 311 for adherence therebetween so that the substrates and elastic members together pass through the nip 309.

The apparatus 201 are each operated as described above to guide the elastic members 61 onto the substrates 303, 311 along a desired securement path 63, and in a desired pattern within the securement path. For example, the guide plates 225 of each apparatus 201 are moved laterally relative to the flow direction F of the substrates 303, 311 to vary the securement paths 63 of the elastic members 61 laterally relative to the flow direction F of the substrates generally in accordance with the contour of the side edges 31 of the training pants 21. The control system 212 is operated to move the guides 253 of each apparatus 201 laterally relative to the flow direction F of the substrates 303, 311 to alter the transverse position of the elastic member within the securement path 63.

For example, to guide the elastic members 61 onto the substrates 303, 311 in a generally periodic pattern along the securement path 63, the control system operates the drive mechanism to oscillate one drive assembly gear 209a of each apparatus 201 through clockwise and counter-clockwise rotations corresponding to the desired shape and period of the pattern. In accordance with operation of the apparatus 201 as described previously, the guides 253 of each apparatus are thus oscillated through movements laterally relative to the flow direction F of the substrates 303, 311, and more particularly transverse to the securement path 63, to guide the elastic members 61 onto the substrates in accordance with the desired pattern. As the elastic members 61 are guided onto the substrates 301, 311, the elastic members are adhered between the substrates. Subsequently passing the substrates 303, 311 and elastic members 61 through the nip 307 serves to further secure the elastic members between the substrates and can further serve to secure the substrates together. However, the step of passing the substrates through the nip may be omitted without departing from the scope of this invention.

The amplitude of the periodic wave pattern defined by each elastic member 61 is generally a function of the radial spacing of the outer pulley 249 from the inner pulley 247 on the positioning arm 241 and the angle through which the positioning arm is pivoted. The period of the periodic wave pattern is generally a function of the rate at which the substrates 303, 311 are fed in the flow direction thereof to the nip 307 and the rate at which the positioning arm 241 is pivoted relative to the flow direction of the substrate. The slope S (FIG. 4A) defined by the elastic member 61 as it extends transversely within the width W of the securement path 63 thereof is determined by controlling one or more of the rate at which the substrates are fed through the nip 307, the transverse positioning of the guide relative to the flow direction F of the substrates and the rate at which the guide is moved relative to the flow direction of the substrates.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A disposable absorbent article comprising a liner adapted for contiguous relation with the wearer's skin, an outer cover, an absorbent body between the liner and the outer cover for absorbing liquid body waste, and at least one elastic member secured within the article along a generally crooked securement path, the position of said at least one elastic member varying transversely within the securement path to at least partially define a width of said securement path.

2. A disposable absorbent article as set forth in claim 1 wherein said article has a longitudinal axis, longitudinally opposite ends and laterally opposite side edges, said securement path being a first securement path extending longitudinally intermediate said longitudinal ends generally adjacent one of said side edges and being generally crooked relative to the longitudinal axis of the article, said article further comprising at least one other elastic member secured within the article along a second securement path extending longitudinally intermediate said longitudinal ends generally adjacent the opposite one of said side edges, said second securement path being generally crooked relative to the longitudinal axis of said article, the position of the at least one other elastic member varying transversely within the second securement path.

3. A disposable absorbent article as set forth in claim 2 wherein at least a portion of each of side edge of the article is oblique relative to the longitudinal axis of the article to define a contour of each side edge, said first and second securement paths having shapes corresponding to the contours of the respective side edges of the article.

4. A disposable absorbent article as set forth in claim 1 wherein the securement path has a length, the position of said at least one elastic member varying transversely within the securement path in a generally periodic wave pattern having at least one period within said securement path, said periodic wave pattern being shaped such that said article is more stretchable generally in the direction of the securement path than transverse to the securement path.

5. A disposable absorbent article as set forth in claim 1 wherein the securement path has a length, the position of said at least one elastic member varying transversely within the securement path in a generally periodic wave pattern, said periodic wave pattern having at least two periods within the length of the securement path.

6. A disposable absorbent article comprising a liner adapted for contiguous relation with the wearer's skin, an outer cover, an absorbent body between the liner and the outer cover for absorbing liquid body waste, and at least one elastic member secured within the article along a securement path, the position of said at least one elastic member varying transversely within the securement path in a generally periodic wave pattern having at least one period within said securement path, said periodic wave pattern being shaped such that said article is more stretchable in the direction of the securement path than transverse to the securement path.

7. A disposable absorbent article as set forth in claim 6 wherein the securement path has a length, and the periodic wave pattern of the at least one elastic member has at least two periods within the length of the securement path.

8. A method of forming an elastic composite comprising the steps of:

moving a substrate in a flow direction thereof;

guiding an elongate elastic member onto the substrate and securing the elastic member to the substrate along a securement path, said guiding step comprising varying the lateral position of the elastic member relative to the flow direction of the substrate to vary the position of the elastic member transversely within the securement path in a generally periodic wave pattern wherein the periodic wave pattern is shaped such that the formed elastic composite is more stretchable in the direction of the securement path than transverse to the securement path.

9. A method as set forth in claim 8 wherein said guiding step further comprises controlling at least one of a speed at which the substrate moves in the flow direction, and the lateral position of the elastic member relative to the flow direction of the substrate, such that the periodic wave pattern is shaped such that the formed elastic composite is more stretchable in the direction of the securement path than transverse to the securement path.

10. A method as set forth in claim 8 further comprising passing the substrate through a roller nip after the elastic member is guided onto the substrate to further adhere the elastic member to the substrate.

11. A method of forming an elastic composite, the method comprising the steps of:

moving a substrate in a flow direction thereof;

guiding an elongate elastic member onto the substrate along a securement path, at least a portion of the securement path being oblique relative to the flow direction of the substrate, said guiding step comprising varying the lateral position of the elastic member relative to the flow direction of the substrate to vary the position of the elastic member transversely within the securement path; and securing the elastic member to the substrate.

12. A method as set forth in claim 11 wherein said varying step comprises varying the lateral position of the elastic member relative to the flow direction of the substrate in a generally periodic wave pattern.

13. A method of forming an elastic composite comprising the steps of:

moving a substrate in a flow direction thereof;

guiding an elongate elastic member onto the substrate and securing the elastic member to the substrate along a securement path, said guiding step comprising varying the lateral position of the elastic member relative to the flow direction of the substrate to vary the position of the elastic member transversely within the securement path in a generally periodic wave pattern wherein the periodic wave pattern is shaped such that the formed elastic composite is more stretchable in the direction of the securement path than transverse to the securement path;

controlling at least one of a speed at which the substrate moves in the flow direction, and the lateral position of the elastic member relative to the flow direction of the substrate, at least one of the speed at which the substrate moves in the flow direction, and the lateral positioning of the elastic member relative to the flow direction of the substrate, is controlled such that the elastic member has a slope of between about −1 and about 1 relative to the flow direction of the securement path.

14. A disposable absorbent article as set forth in claim 3 wherein said article is a child's toilet training pants comprising an anterior region, a posterior region and a crotch region disposed longitudinally therebetween, said anterior region, posterior region and crotch region being integrally formed and configured to have a central waist opening generally defined by said longitudinal ends and a pair of leg openings defined by said laterally opposite side edges.

* * * * *